(12) United States Patent
Uchida et al.

(10) Patent No.: US 9,061,105 B2
(45) Date of Patent: Jun. 23, 2015

(54) NEEDLE ASSEMBLY

(75) Inventors: Yoshikuni Uchida, Gunma-ken (JP);
Youta Sekiduka, Gunma-ken (JP);
Hirokazu Sutou, Gunma-ken (JP)

(73) Assignee: NIPRO CORPORATION, Osaka-shi (JP)

( * ) Notice: Subject to any disclaimer, the term of this patent is extended or adjusted under 35 U.S.C. 154(b) by 478 days.

(21) Appl. No.: 12/737,093

(22) PCT Filed: Jun. 11, 2009

(86) PCT No.: PCT/JP2009/060684
§ 371 (c)(1),
(2), (4) Date: Dec. 7, 2010

(87) PCT Pub. No.: WO2009/154131
PCT Pub. Date: Dec. 23, 2009

(65) Prior Publication Data
US 2011/0077600 A1     Mar. 31, 2011

(30) Foreign Application Priority Data

Jun. 20, 2008 (JP) ................. 2008-161982

(51) Int. Cl.
*A61M 5/32* (2006.01)

(52) U.S. Cl.
CPC ............. *A61M 5/326* (2013.01); *A61M 5/3202* (2013.01); *A61M 5/3272* (2013.01); *A61M 2005/3267* (2013.01)

(58) Field of Classification Search
CPC .................... A61M 5/326; A61M 2005/3267; A61M 5/3202
USPC .................... 604/110, 192, 198, 263, 164.01, 604/164.04, 164.08
See application file for complete search history.

(56) References Cited

U.S. PATENT DOCUMENTS

| 4,775,369 A | * | 10/1988 | Schwartz | 604/263 |
| 4,813,426 A | * | 3/1989 | Haber et al. | 600/576 |
| 5,104,384 A | * | 4/1992 | Parry | 604/192 |

FOREIGN PATENT DOCUMENTS

| WO | WO 01/91837 | 12/2001 |
| WO | WO 03/045480 | 6/2003 |
| WO | WO 2008/028304 | 3/2008 |

* cited by examiner

*Primary Examiner* — Edelmira Bosques
(74) *Attorney, Agent, or Firm* — Flynn, Thiel, Boutell & Tanis, P.C.

(57) ABSTRACT

A needle assembly 1 includes a hub 4 retaining a cannula 3, a protective unit 5 advancing and retracting to surround the forward end of the cannula 3, and a cylindrical portion 6 surrounding the outer periphery of the protective unit 5; the protective unit 5 has a construction in which a protective cover 7 protruding from and retracting into the cylindrical portion 6 is formed integrally with a spring portion 8 so as to be in series therewith, with the hub 4 and the cylindrical portion 6 being coupled together to form a hub member.

7 Claims, 9 Drawing Sheets

FIG. 5
(a) 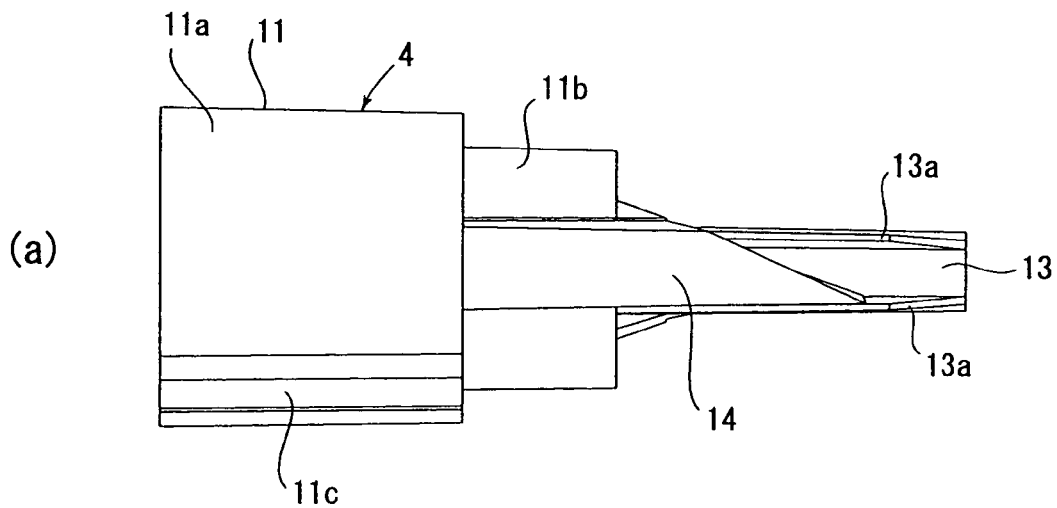
(b) 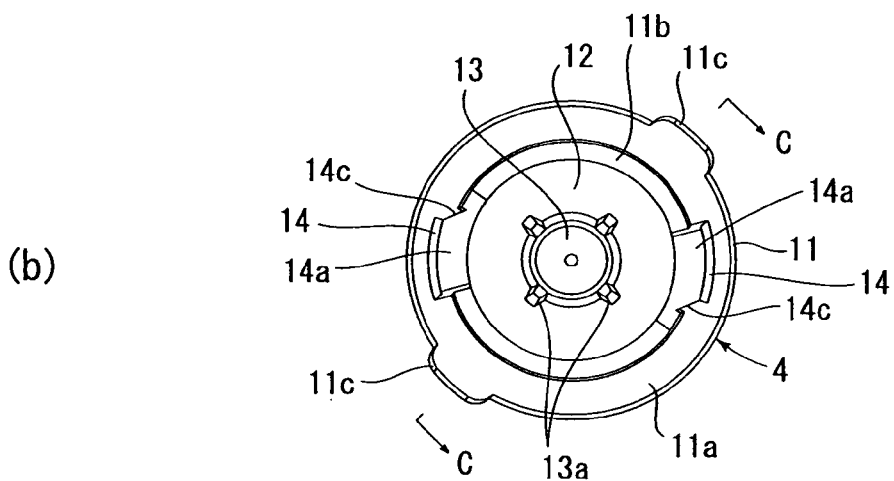
(c) 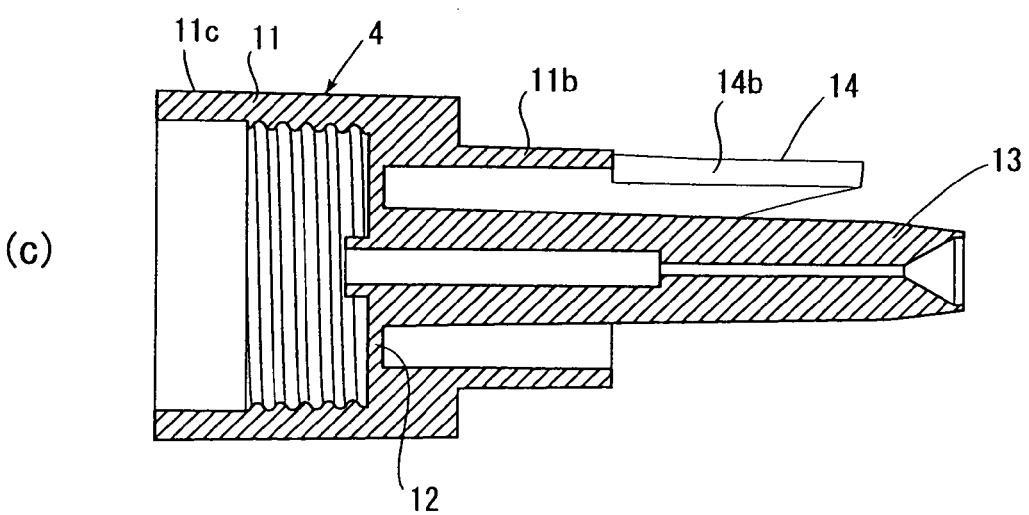

FIG. 6
(a) 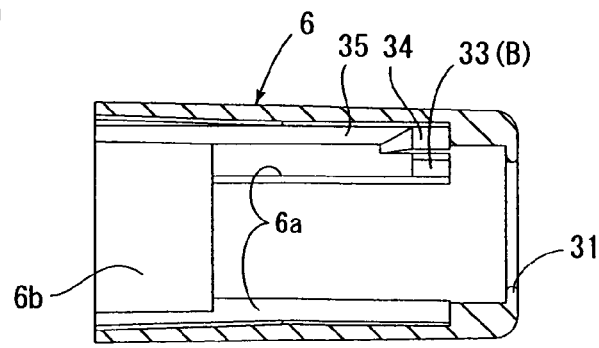
(b) 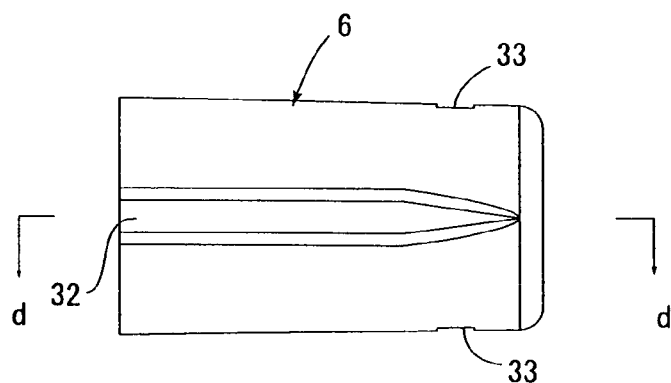
(c) 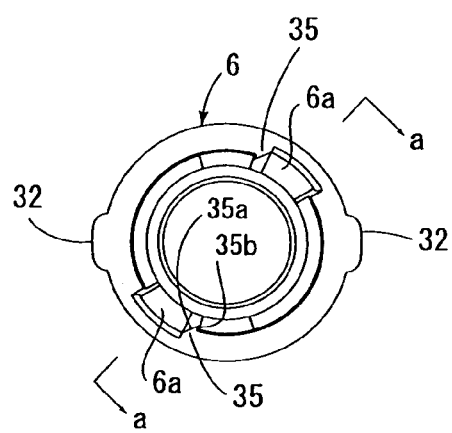
(d) 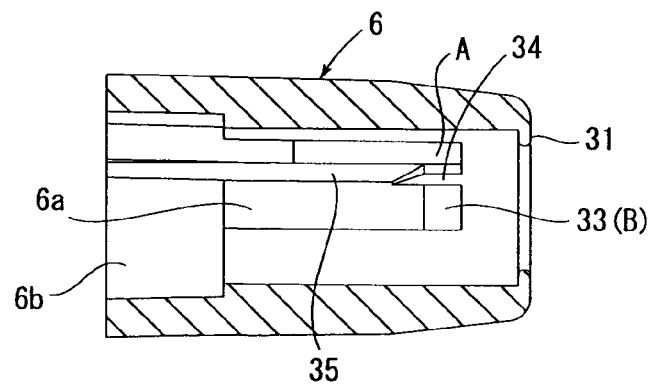

NEEDLE ASSEMBLY

TECHNICAL FIELD

The present invention relates to a needle assembly and, more specifically, to a needle assembly equipped with a protective cover moving to an advanced position where it surrounds the forward end of a cannula and to a retracted position where it exposes the forward end of the cannula.

BACKGROUND ART

Conventionally, there has been known a needle assembly comprising a hub retaining a cannula, a protective cover advancing and retracting with respect to the hub to be situated at an advanced position where it surrounds the forward end of the cannula and a retracted position where it exposes the forward end of the cannula, an urging means elastically provided between the hub and the protective cover and urging the protective cover forwards, and a stopper means retaining the protective cover at the advanced position.

Further, as an example of such a needle assembly, there is also known a needle assembly in which the protective cover is moved to be placed in a pre-use state in which it is situated at the advanced position to surround the forward end of the cannula, a use state in which the protective cover is situated at the retracted position to expose the forward end of the cannula, and a post-use state in which it is again situated as the advanced position to surround the forward end of the cannula and in which it is fixed in position so that it may not move to the retracted position again (Patent Documents 1 and 2).

The insulin injection system of Patent Document 1 is composed of the above-mentioned hub, the protective cover provided so as to cover the outer peripheral surface of the hub, and a spring member provided inside the hub and abutting the forward end side bottom portion of the protective cover.

In the insulin injection system of Patent Document 1, an engagement protrusion is provided on the inner peripheral surface of the protective cover, and a guide groove guiding the engagement protrusion is provided in the outer peripheral surface of the hub.

When the protective cover in the pre-use state is pressed backwards, this guide groove guides the engagement protrusion backwards, and, when the cannula is placed in the use state, it moves forwards while rotating along a groove formed obliquely forwards to be placed in the post-use state.

In the post-use state, a protrusion is fit-engaged with a recess formed in the guide groove, preventing the protective cover from moving backwards again.

The injection needle structure of Patent Document 2 is composed of a cylindrical portion surrounding the outer periphery of the protective cover in front of the hub, a fixation member provided at the rear of the protective cover, and a spring member elastically provided between the fixation member and the hub.

In the injection needle structure of Patent Document 2, a protrusion is provided on each of the inner peripheral surface of the cylindrical portion, the outer peripheral surface of the protective cover, and the outer peripheral surface of the fixation member, with these protrusions being inclined as appropriate.

Thus, when the protective cover is retracted from the pre-use state, the protective cover rotates to be placed in the use state, with the inclined surfaces of the protrusions sliding on each other; thereafter, when the protective cover moves forwards, the protective cover rotates to be placed in the post-use state, with the inclined surfaces of the protrusions further sliding on each other.

In this post-use state, the protrusions are held in contact with each other, preventing the protective cover from retracting.

PRIOR ART DOCUMENTS

Patent Documents

Patent Document 1: JP-T-2003-534105
Patent Document 2: JP-T-2005-510308

SUMMARY OF THE INVENTION

Problems that the Invention is to Solve

However, in the insulin injection system of Patent Document 1, the protective cover is formed so as to cover the outer periphery of the hub, so that it is rather difficult to operate the syringe while retaining this protective cover.

Further, in the insulin injection system of Patent Document 1, when placing it in the post-use state from the use state, it is necessary to obliquely move the engagement protrusion along the guide groove; however, since the urging force of the spring is exerted straight forwards, there is the possibility of its being allowed to move to the pre-use position again.

On the other hand, in the case of the injection needle structure of Patent Document 2, it is necessary to provide a large number of components, resulting in a high production cost.

In view of the above problems, the invention aims to provide a needle assembly which can be produced at low cost and which can be used safely.

Means for Solving the Problems

According to (1) of the invention, there is provided a needle assembly comprising: a hub retaining a cannula; a protective cover advancing and retracting with respect to the hub to be situated at an advanced position where it surrounds the forward end of the cannula and a retracted position where it exposes the forward end of the cannula; an urging means elastically provided between the hub and the protective cover and forwardly urging the protective cover; and a stopper means retaining the protective cover at the advanced position, characterized in that the hub is provided with a cylindrical portion surrounding an outer periphery of the protective cover, and that a spring portion as the urging means is provided so as to be aligned in series with the protective cover, with the protective cover and the spring portion being integrally formed of an elastic material.

According to (2) of the invention, there is provided a needle assembly comprising: a hub retaining a cannula; a protective cover advancing and retracting with respect to the hub to be situated at an advanced position where it surrounds the forward end of the cannula and a retracted position where it exposes the forward end of the cannula; an urging means elastically provided between the hub and the protective cover and forwardly urging the protective cover; and a stopper means retaining the protective cover at the advanced position, the protective cover being moved to be placed in a pre-use state in which the protective cover is situated at the advanced position to surround the forward end of the cannula, a use state in which the protective cover is situated at the retracted position to expose the forward end of the cannula, and a post-use state in which it is situated again at the advanced position to surround the forward end of the cannula and fixed in position so as not to be allowed to move to the retracted position again, characterized in that the hub is provided with a cylindrical portion surrounding an outer periphery of the protective cover, one of a hub member formed by the hub and the cylindrical member and the protective cover being provided with an engagement protrusion, the other being provided with a guide means regulating movement of the engagement protrusion, that the guide means is provided with a pre-use retaining portion retaining the engagement protrusion at the position of the pre-use state, a post-use retaining portion fixing the engagement protrusion at the position of the post-use state, and an inclined surface engaged with the engagement protrusion when the protective cover is retracted and causing the protective cover to retract while causing it to rotate from the pre-use retaining portion side position toward the post-use retaining portion side position, and that, when the protective cover is caused to retract against the urging force of the urging means from the pre-use state, the engagement protrusion and the inclined surface are brought into contact with each other, and, when the protective cover retracts while rotating to be placed in the use state, and the protective cover is caused to advance from the use state, the engagement protrusion is fixed to the post-use retaining portion to be placed in the post-use state.

Advantage of the Invention

According to the invention of (1), the cylindrical portion is provided so as to surround the protective cover, whereby the user can give an injection while holding this protective cover.

Further, since the protective cover and the spring portion are formed integrally of an elastic material, it is possible to reduce the number of components as compared with Patent Documents 1 and 2, and, further, since the protective cover and the spring portion are aligned in series, they can be easily formed integrally, and the needle assembly can be reduced in size.

That is, if the protective cover and the spring portion are formed separately, it is necessary to form a spring receiving portion on the protective cover, and the size of the protective cover becomes so much the larger and, by extension, the size of the entire needle assembly increases.

According to the invention of (2), the cylindrical portion is provided so as to surround the protective cover, so that the user can give an injection while holding this protective cover.

Further, when moving the protective cover from the pre-use position to the use position, the protective cover retracts while rotating, so that, when moving from the use position to the post-use position afterwards, it is moved forwards by the urging force of the urging means.

That is, the engagement protrusion is not easily allowed to rotate to move to the pre-use retaining portion side, thereby preventing a malfunction.

Further, as compared with the injection needle structure of Patent Document 2, it is possible to reduce the number of components, making it possible to produce the needle assembly at low cost.

BRIEF DESCRIPTION OF THE DRAWINGS

FIG. 5 Diagrams illustrating a main body portion, of which portion (a) is a side view as seen from the direction V-V of FIG. 1, portion (b) is a front view of portion (a), and portion (c) is a sectional view taken along the line c-c of portion (b).

FIG. 6 Diagrams illustrating a cylindrical portion, of which portion (a) is a sectional view as seen from the same direction as in FIG. 1, portion (b) is a side view as seen from the direction V-V of FIG. 1, portion (c) is a front view of portion (a), and portion (d) is a sectional view taken along the line d-d of portion (b).

MODE FOR CARRYING OUT THE INVENTION

Figure 1:
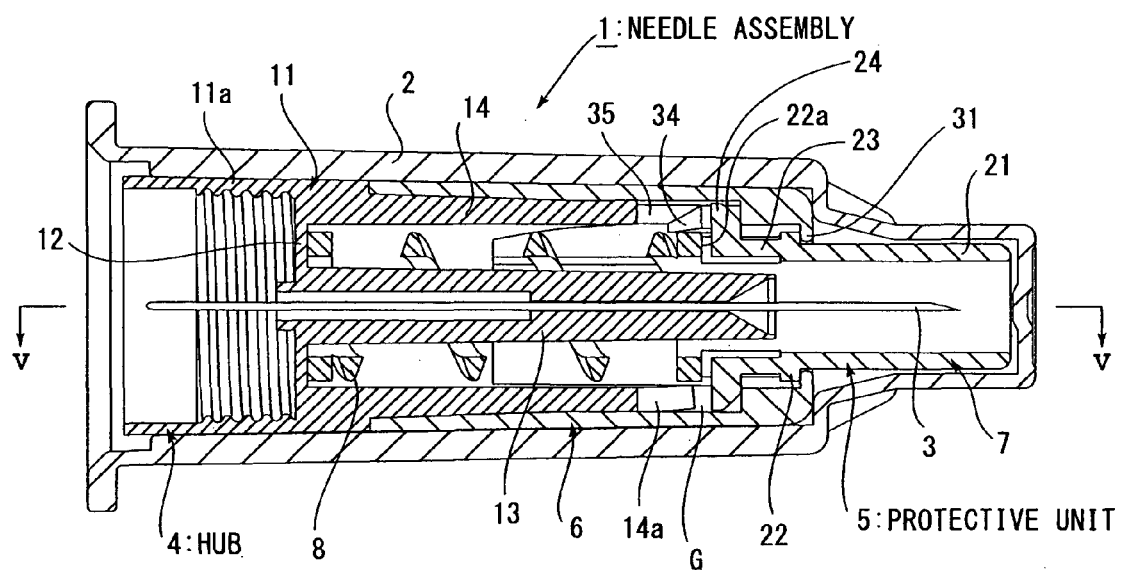
FIG. 1 A sectional view of a needle assembly according to a first embodiment in a pre-use state.
Figure 2:
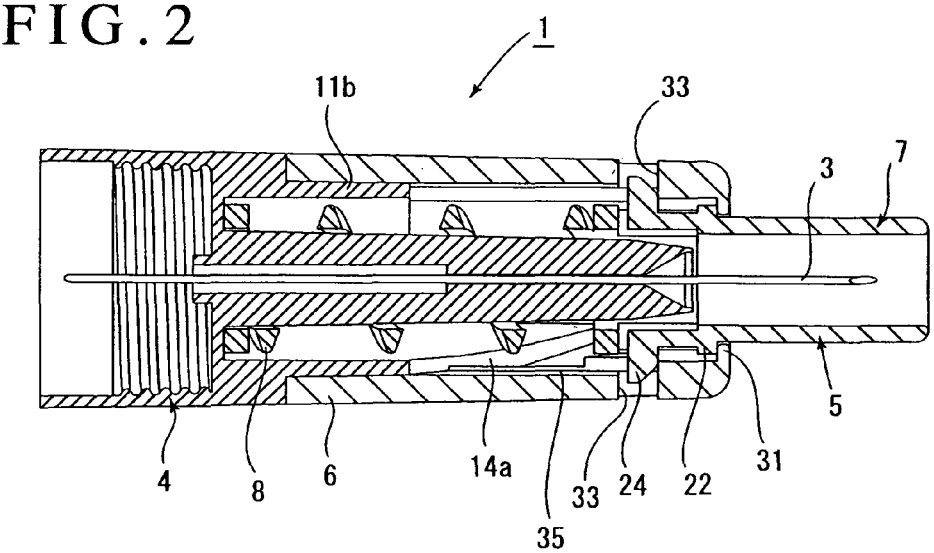
FIG. 2 A sectional view of the needle assembly in a post-use state.
Figure 3:
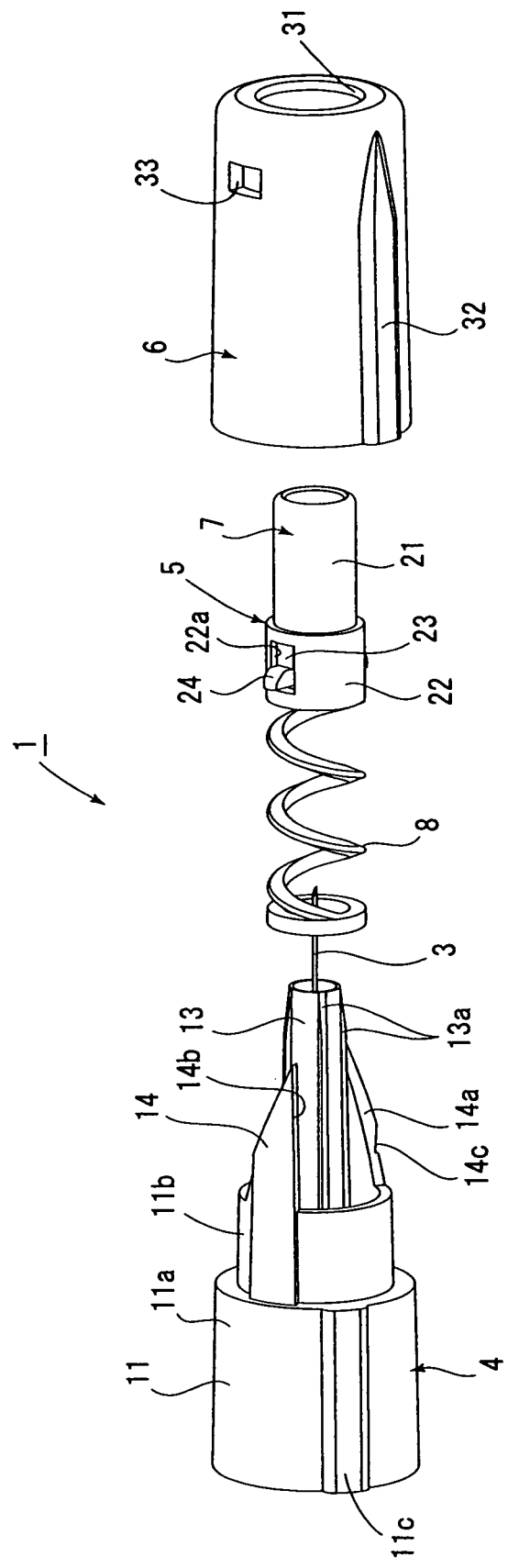
FIG. 3 A diagram illustrating the components of the needle assembly.

In the following, the embodiments shown in the drawings will be described; FIGS. 1 through 3 illustrate a needle assembly 1 for insulin injection according to the first embodiment; FIG. 1 shows the needle assembly 1 in the pre-use state; FIG. 2 shows the needle assembly 1 in the post-use state; FIG. 3 is an exploded view of the needle assembly 1; a container cap 2 for use during storage and transport is attached to the needle assembly 1 of FIG. 1.

The needle assembly 1 is attached to the forward end of a cartridge containing insulin (not shown); in the following description, "forwards" or "forward end" means the right-hand side in FIGS. 1 and 2, i.e., the patient side, and "rearwards" or "rear end" means the left-hand side as seen in the drawing, i.e., the cartridge side.

The needle assembly 1 is composed of a hub 4 retaining a cannula 3, a protective unit 5 advancing and retracting with respect to the hub 4 to surround the forward end of the cannula 3, and a cylindrical portion 6 connected to the front side of the hub 4 and surrounding the outer periphery of the protective unit 5.

Of these, the protective unit 5 is composed of a protective cover 7 protruding from and retracting into the cylindrical portion 6, and a spring portion 8 provided in series at the rear end of the protective cover 7, the hub 4 and the cylindrical portion 6 being connected to constitute a hub member.

Figure 4:
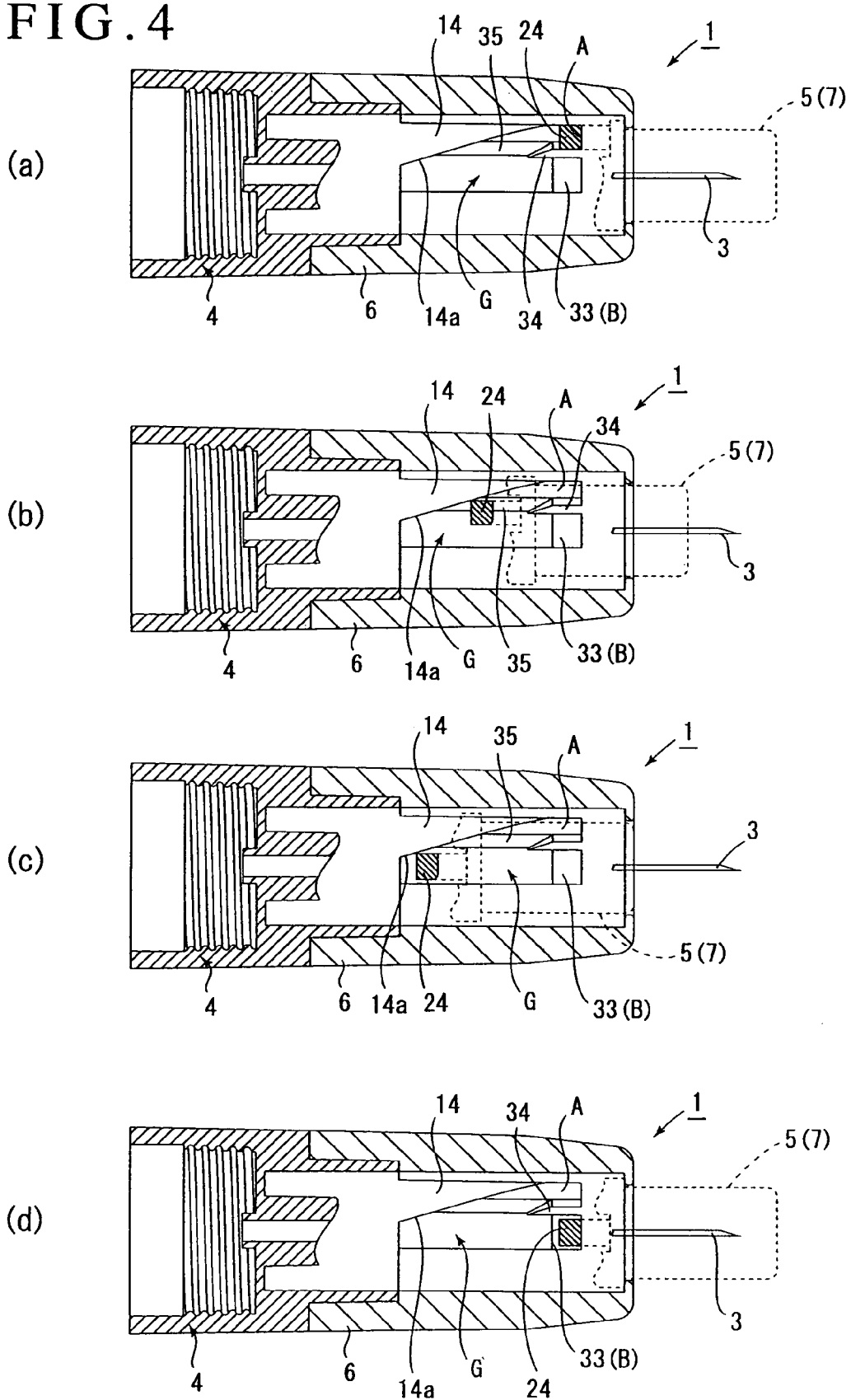
FIG. 4 Diagrams illustrating the operation of the needle assembly, of which portion (a) illustrates the pre-use state, portion (b) illustrates an intermediate state between the pre-use state and the use state, portion (c) illustrates the use state, and portion (d) illustrates the post-use state.

As shown in the portions of FIG. 4, the needle assembly 1 of this embodiment can be placed in a pre-use state in which the forward end of the protective unit 5 is situated at an advanced position (FIG. 4(*a*)), a use state in which the forward end of the protective unit 5 has moved to a retracted position and in which the cannula 3 can be pierced into the patient (FIG. 4(c)), and a post-use state in which the forward end of the protective unit 5 is situated at the advanced position again (FIG. 4 (d)).

And, when the needle assembly has been placed in the post-use state, the protective unit 5 is fixed to the hub member and cannot retract thereafter, whereby re-use of the needle assembly 1 is prevented, and it is possible to prevent erroneous piercing due to the exposure of the cannula 3.

FIGS. 5(a) through 5(c) show the hub 4, of which FIG. 5(a) is a side view of the hub 4 as seen from the direction V-V of FIG. 1, FIG. 5(b) is a front view of FIG. 5(a), and FIG. 5(c) is a sectional view taken along the line c-c of FIG. 5(b).

The hub 4 is composed of a cylindrical base portion 11 connected to the cartridge, a bottom portion 12 provided substantially at the center in the longitudinal direction of the base portion 11, a retaining portion 13 protruding forwards from the center of the bottom portion 12 to retain the cannula 3, and two guide portions 14 protruding forwards from the base portion 11.

In the inner peripheral surface at the rear of the bottom portion 12 of the base portion 11, there is formed a screw portion threadedly engaged with the cartridge, and the rear end of the spring portion 8 of the protective unit 5 abuts the front side of the bottom portion 12 (See FIG. 1).

The base portion 11 is composed of a large diameter portion 11a formed to extend somewhat forwardly beyond the bottom portion 12, a small diameter portion 11b formed in front of the large diameter portion 11a, and two swollen portions 11c provided on the outer peripheral surface of the large diameter portion 11a.

The retaining portion 13 protrudes forwards from the center of the bottom portion 12, and four ribs 13a are formed on the outer periphery thereof to extend in the longitudinal direction. The cannula 3 extends through the retaining portion 13 in the longitudinal direction, and the rear end thereof is situated between the bottom portion 12 and the rear end of the base portion 11.

The two guide portions 14 have a substantially wedge-shaped configuration protruding forwards from the small diameter portion 11b of the base portion 11, and include an inclined surface 14a inclined from the front side toward the rear side and a vertical surface 14b formed to extend straight in the longitudinal direction.

Further, a part of the outer peripheral surface of the guide portion 14 swells to a substantially intermediate position between the large diameter portion 11a and the small diameter portion 11b, and has an engagement groove 14c formed in the longitudinal direction, which is to be fit-engaged with a return prevention protrusion 35 formed on the cylindrical portion 6 described below.

The protective unit 5 is formed integrally of an elastic resin; it is formed such that the retaining portion 13 of the hub 4 extends through the centers of the protective cover 7 and the spring portion 8.

The protective cover 7 is composed of a cover portion 21 provided so as to be capable of protruding from and retracting into the hub 4, and an engagement portion 22 provided at the rear of the cover portion 21, with a step being formed at the boundary between the cover portion 21 and the engagement portion 22. This step constitutes an engagement surface forming a stopper means for retaining the protective cover 7 at the advanced position.

Further, the side surface of the engagement portion 22 has two through-holes 22a at opposing positions, and, inside the through holes 22a, there is provided an engagement protrusion 24 through the intermediation of a deformation portion 23.

The engagement protrusion 24 normally protrudes outwards beyond the outer peripheral surface of the engagement portion 22; when the engagement protrusion 24 is pressed from the outer peripheral side, the deformation portion 23 is deformed and moves to the cannula 3 side; when the pressing force is released, it is restored to the former position.

The spring portion 8 is connected in series to the rear end of the engagement portion 22, and the rear end thereof abuts the bottom portion 12 of the hub 4 to urge the protective cover 7 forwards.

Due to the construction in which the spring portion 8 is connected in series to the rear end of the protective cover 7, the protective cover 7 and the spring portion 8 easily allow integral formation, making it possible to reduce the size of the needle assembly and facilitating the handling thereof.

More specifically, when the protective cover and the spring portion are formed as separate components, it is necessary to form on the protective cover a spring receiving portion for retaining the spring portion, which not only complicates the structure of the protective cover, but also leads to an increase in the size of the needle assembly as a whole since it is necessary to make the diameter of the protective cover larger or to lengthen the entire length, making the needle assembly rather difficult to handle.

FIGS. 6(a) through 6(d) show the cylindrical portion 6, of which FIG. 6(a) is a sectional view as seen from the same direction as in FIG. 1, FIG. 6(b) is a side view of the cylindrical portion 6 as seen from the direction V-V of FIG. 1, FIG. 6(c) is a front view of FIG. 6(a), and FIG. 6(d) is a sectional view taken along the line d-d of FIG. 6(b). FIG. 6(a) is a sectional view taken along the line a-a of FIG. 6(c).

At the forward end of the cylindrical portion 6, there is provided a flange 31 swollen toward the inner peripheral side; further, on the outer peripheral surface, there are provided two swollen portions 32 at opposing positions, and two through-holes 33 are provided at positions rotated by 90° with respect to the swollen portions 32.

The flange 31 is substantially of the same diameter as the cover portion 21 of the protective cover 7, and the rear surface of the flange 31 abuts the engagement portion 22 of the protective cover 7 to constitute a surface to be engaged of a stopper means retaining the protective cover 7 at the advance position.

The engagement protrusion 24 of the protective cover 7 is inserted into the through-holes 33 in the above-mentioned post-use state; at this time, the rear end surface of the engagement protrusion 24 and the through-holes 33 are engaged with each other, with the protective cover 7 being fixed to the hub 4 so as not to be capable of retracting.

And, due to the provision of the swollen portions 32, when the hub 4 is inserted into the cylindrical portion 6 while linearly aligning the swollen portions 32 with the swollen portions 11c of the hub 4, it is possible to easily assemble the hub member.

As shown in FIG. 6(d), in the inner peripheral surface of the cylindrical portion 6, there are formed a groove 6a formed longitudinally at opposing positions with the cannula 3 therebetween, and a step portion 6b fit-engaged with the small diameter portion 11b of the hub 4.

At the forward end of the groove 6a, there is situated the engagement protrusion 24 when the protective cover 7 is situated at the advanced position, with the rear end thereof being open as it is to the above-mentioned step portion 6b.

At the center of the forward end portion of the groove 6a, there is provided a rotation preventing protrusion 34 protruding on the inner peripheral surface side, and a return prevention protrusion 35 is formed at the rear of the rotation preventing protrusion 34, the above-mentioned through-holes 33 being situated at lower positions as seen in the drawing adjacent to the rotation preventing protrusion 34.

The width on the upper side as seen in the drawing and on the lower side as seen in the drawing of the rotation preventing protrusion 34 in the above-mentioned groove 6a is a width allowing movement of the engagement protrusion 24 of the protective cover 7; further, as compared with the inner peripheral surface on the upper side as seen in the drawing, the inner peripheral surface on the lower side as seen in the drawing is formed somewhat shallower.

Figure 7:
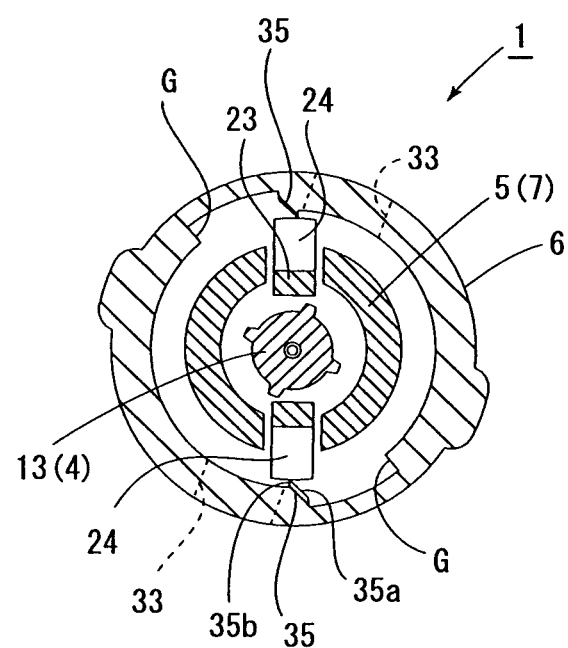
FIG. 7 A diagram illustrating the relationship between an engagement protrusion and a guide means in FIG. 4(*b*).

As shown in FIG. 7, the return prevention protrusion 35 is composed of an inclined portion 35a gradually protruding on the inner peripheral surface side from a pre-use retaining portion A toward a post-use retaining portion B, and a step portion 35b formed at a position of the inclined portion 35a adjacent to the post-use retaining portion B side.

And, on the inner peripheral surface of the hub member composed of the hub 4 and the cylindrical portion 6, there is formed a guide means G regulating the movement of the engagement protrusion 24 of the protective cover 7.

More specifically, when the hub 4 and the cylindrical portion 6 are connected with each other, the vertical surface 14b of the guide portion 14 of the hub 4 is brought into intimate contact with the side surface of the groove 6a of the cylindrical portion 6; and, further, the return prevention protrusion 35 of the cylindrical portion 6 and the engagement groove 14c of the guide portion 14 are mutually fit-engaged with each other.

As a result, as shown in the portions of FIG. 4, above the rotation preventing protrusion 34 in the groove 6a, there is formed the pre-use retaining portion A retaining the engagement protrusion 24 in the pre-use state, and, in the through-hole 33 below the rotation preventing protrusion 34 as seen in the drawing, there is formed the post-use retaining portion B engaged with the engagement protrusion 24 in the post-use state.

And, the inclined surface 14a of the guide portion 14 of the hub 4 is situated at the rear of the pre-use retaining portion A and the post-use retaining portion B; further, the inclined surface 14a is inclined backwards from the pre-use retaining portion A side toward the post-use retaining portion B side.

In the following, the handling of the needle assembly 1 constructed as described above will be illustrated.

First, a cartridge containing insulin contains insulin for a plurality of injections, and a new needle assembly 1 must be attached to this cartridge each time an insulin injection is given.

As shown in FIG. 1, at the time of storage, the container cap 2 is attached to the needle assembly 1, and the container cap 2 is sealed by a film (not shown) to prevent intrusion of germs, etc. into the interior.

When using the needle assembly 1, the film is first removed from the container cap 2, and, in this state, a cartridge or a pen-type syringe is attached to the base portion 11 of the hub 4, whereby the rear end portion of the cannula 3 protruding into the interior of the base portion 11 is pierced into the forward end of the cartridge or the pen-type syringe.

After this, by removing the container cap 2, the needle assembly 1 is exposed to the exterior, and the needle assembly 1 is placed in the pre-use state shown in FIG. 4(a).

At this time, the protective cover 7 is forwardly urged by the urging force of the spring portion 8, and the engagement portion 22 abuts the flange 31 of the cylindrical portion 6 from behind, with the protective cover 7 being situated at the advanced position to surround the cannula 3.

The engagement protrusion 24 of the protective cover 7 is situated at the pre-use retaining portion A of the guide means G, and is prevented from rotating to the post-use retaining portion B side by the rotation preventing protrusion 34.

Next, in the state of FIG. 4(a), the patient himself or the medical worker (hereinafter referred to as the user) presses the syringe substantially vertically against the skin of the patient while grasping the cylindrical portion 6; then, the protective cover 7 retracts with respect to the hub 4 against the urging force of the spring portion 8, and the forward end of the cannula 3 is somewhat exposed as shown in FIG. 4(b).

Here, when the protective cover 7 is pressed against the skin of the patient, the protective cover 7 retracts straight backwards at first; and, immediately after this, the engagement protrusion 24 abuts the inclined surface 14a of the guide means G from the front side.

Then, the engagement protrusion 24 of the protective cover 7 moves obliquely backwards along the inclined surface 14a, and, at the same time, the entire protective unit 5 rotates around the cannula 3.

Further, as shown in FIG. 7, the engagement protrusion 24 abuts the return prevention protrusion 35 of the guide means G, so that the deformation portion 23 undergoes deformation, and the engagement protrusion 24 moves to the cannula 3 side.

When, from the state of FIG. 4(b), the needle assembly 1 is further pressed to the patient side, the protective cover 7 completely retracts, and the cannula 3 is completely exposed, resulting in the use state as shown in FIG. 4(c).

At this time, the protective cover 7 further retracts against the urging force of the spring portion 8, and, at the same time, the engagement protrusion 24 further moves obliquely backwards while rotating along the inclined surface 14a, and the protective unit 5 as a whole rotates around the cannula 3.

And, when the forward end of the protective cover 7 retracts to the forward end of the cylindrical portion 6 to reach the retracted position, the engagement protrusion 24 gets over the return prevention protrusion 35, and the engagement protrusion 24 is caused to protrude to the outer peripheral side again by the deformation portion 23.

As a result, thereafter, even if an attempt is made to rotate the protective cover 7 to the pre-use retaining portion A side, the engagement protrusion 24 abuts the step portion 35b of the return prevention protrusion 35, so that the rotation to the pre-use retaining portion A side is prevented.

That is, once it is placed in the use state, the needle assembly 1 is not placed in the pre-use state again.

Further, the inner peripheral surface of the guide means G which is on the post-use retaining portion B side of the return prevention protrusion 35 is situated on the cannula 3 side of the inner peripheral surface on the pre-use retaining portion A side, so that the engagement protrusion 24 does not completely protrude from the engagement portion 22, and the deformation portion 23 remains elastically deformed.

And, when the needle assembly 1 is placed in the use state, the user performs a predetermined operation on the cartridge to give an insulin injection; thereafter, he causes the syringe to retract to remove the syringe from the patient, and the needle assembly is placed in the post-use state of FIG. 4(d), in which the protective cover 7 is situated at the advanced position.

At this time, when the syringe is retracted, the protective cover 7 protrudes from the hub 4 due to the urging force of the spring portion 8, and the engagement portion 22 of the protective cover 7 abuts the flange 31 of the cylindrical portion 6 from behind, and is retained at the advanced position.

Here, the spring portion 8 urges the protective cover 7 straight forwards, so that the engagement protrusion 24 moves forwards from the state of FIG. 4(c) to reach the post-use retaining portion B of the guide means G.

Then, the deformation portion 23 is restored to the former configuration, and the engagement protrusion 24 protrudes into the through-hole 33 formed in the cylindrical portion 6, with the rear end of the engagement protrusion 24 abutting the through-hole 33.

As a result, even if the urging force from the front side is exerted to the protective cover 7, it is possible to prevent the protective cover 7 from retracting; further, if an attempt is made to rotate the protective cover 7, the engagement protrusion 24 is engaged with the through-hole 33 and the rotation prevention protrusion 34, so that the engagement protrusion 24 does not rotate to the pre-use retaining portion A side again.

In the needle assembly 1 constructed as described above, once this assembly is placed in the post-use state, the engagement protrusion 24 of the protective cover 7 is immovably fixed by the through-hole 33, so that re-exposure of the cannula 3 is prevented, making it possible to prevent re-use of the needle assembly 1 and erroneous piercing.

Further, since the protective unit 5 is formed as an integral unit, it is possible to reduce the number of components as compared with a conventional needle assembly using a metal spring, and to facilitate the assembly operation.

Further, by arranging the protective cover 7 and the spring portion 8 in series, the configuration formed by coupling together the protective cover 7 and the spring portion 8 does not become complicated, making it possible to easily perform the integral forming and to reduce the size of the needle assembly.

And, when placing the needle assembly in the use state from the pre-use state, the engagement protrusion 24 of the protective cover 7 retracts while rotating due to the inclined surface 14a of the guide means G, and when placing it in the post-use state from the use state, the protective cover 7 moves straight forwards due to the urging force of the spring portion 8, so that it is possible to prevent as much as possible the engagement protrusion 24 from returning to the pre-use retaining portion A after use.

Further, since the return prevention protrusion 35 is provided between the pre-use retaining portion A and the through-hole 33, it is possible to prevent the engagement protrusion 24 from returning to the pre-use retaining portion A, making it possible to guide the engagement protrusion 24 to the through-hole 33 more reliably.

Figure 8:
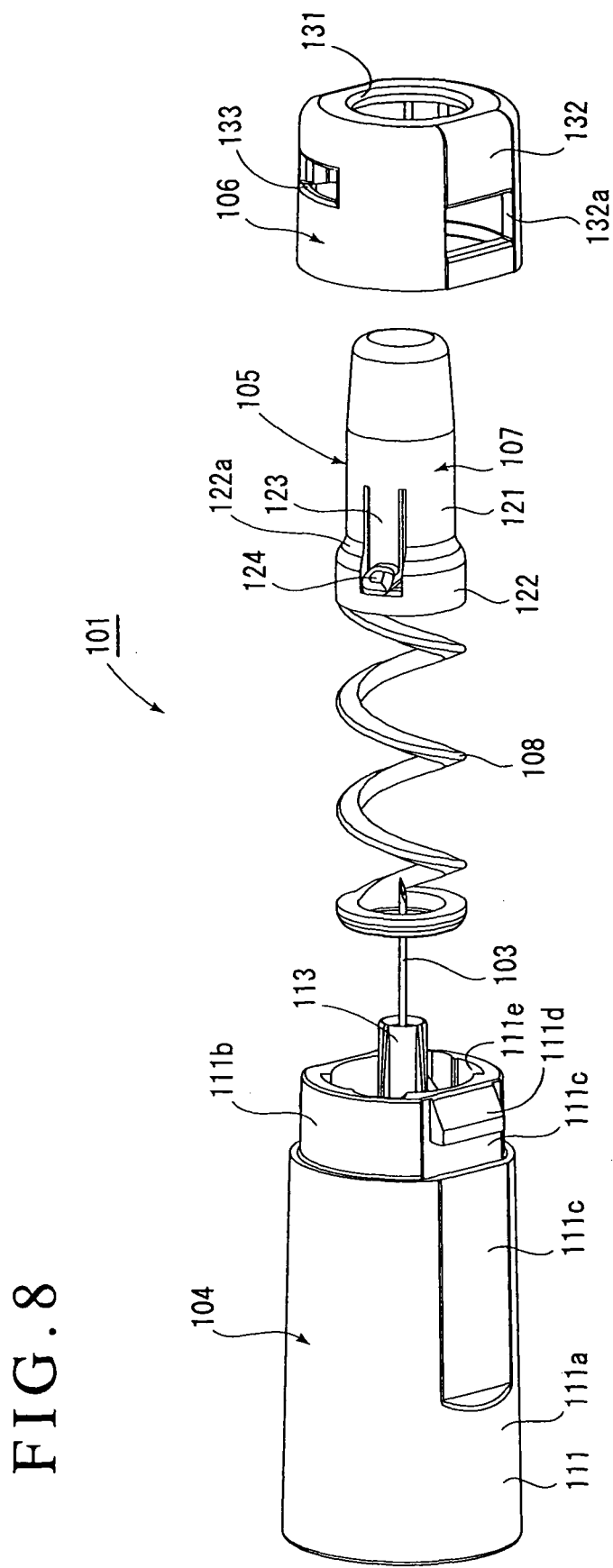
FIG. 8 A diagram illustrating the components of a needle assembly according to a second embodiment.
Figure 9:
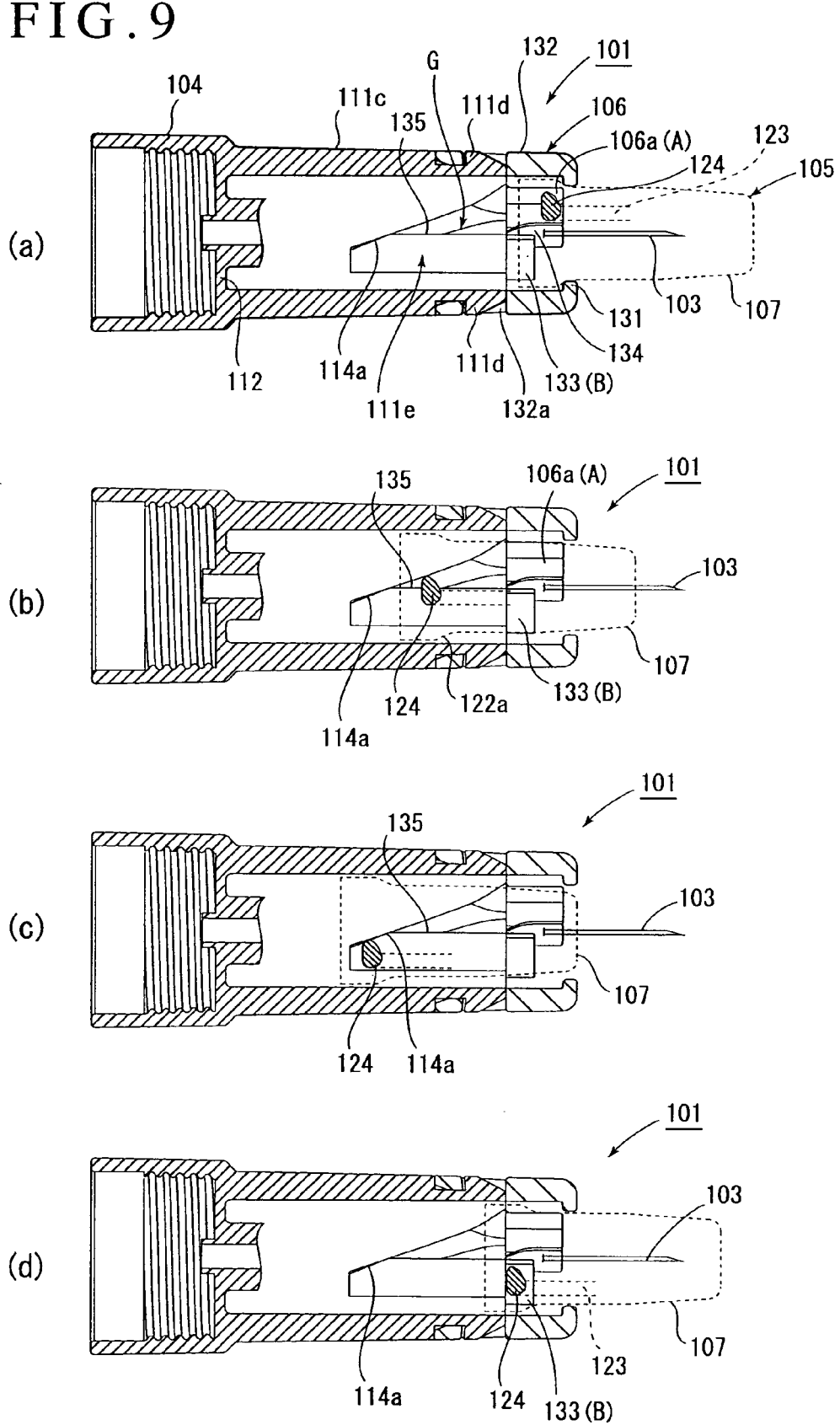
FIG. 9 Diagrams illustrating the operation of the needle assembly of the second embodiment, of which portion (a) illustrates the pre-use state, portion (b) illustrates an intermediate state between the pre-use state and the use state, portion (c) illustrates the use state, and portion (d) illustrates the post-use state.

Next, FIGS. 8 and 9 show a needle assembly 101 according to the second embodiment; in the following description, the members common to those of the needle assembly 1 of the first embodiment are indicated by the same reference numerals, with 100 being added to each reference numeral.

As shown in FIG. 8, the needle assembly 101 is composed of a hub 104 retaining a cannula 103, a protective unit 105 advancing and retracting with respect to the hub 104 to surround the forward end of the cannula 103, and a cylindrical portion 106 connected to the front side of the hub 104 and surrounding the outer periphery of the protective unit 105.

The hub 104 and the cylindrical portion 106 are coupled together to thereby form a hub member, and the inner peripheral surface thereof has a guide means G regulating the movement of an engagement protrusion 124 of the protective cover 107.

In FIG. 9, there are shown a pre-use state in which the forward end of the protective unit 105 is situated at the advanced position (FIG. 9(a)), a state in which an engagement protrusion of the protective unit 105 is situated at a return prevention protrusion (FIG. 9(b)), a use state in which the forward end of the protective unit 105 has been moved to the retracted position, with the cannula 103 allowing piercing into the patient (FIG. 9(c)), and a post-use state in which the forward end of the protective unit 105 is situated at the advanced position again (FIG. 9(d)).

The protective unit 105 is composed of a protective cover 107 protruding from and retracting into the cylindrical portion 106, and a spring portion 108 provided in series at the rear end of the protective cover 107, with the protective cover 107 being provided with an engagement protrusion 124 and a deformation portion 123 retaining the engagement protrusion 124.

The forward end side outer peripheral surface of the protective cover 107 has a tapered configuration, which is tapered toward the forward end; due to this tapered configuration, the forward end of the protective cover 107 can be easily inserted into the cylindrical portion 106 at the time of assembly of the needle assembly 101.

An engagement portion 122 constituting the protective cover 107 is formed to be of a larger diameter than a cover portion 121, and, at the boundary between the engagement portion 122 and the cover portion 121, there is formed an inclined surface 122a constituting an engagement surface as a stopper means retaining the protective cover 107 at the advanced position.

The hub 104 is composed of a cylindrical main body portion 111, a bottom portion 112 provided inside the main body portion 111, and a retaining portion 113 protruding forwards from the center of the bottom portion 112 and retaining the cannula 103.

On the outer peripheral surface of the main body portion 111, there are formed a large diameter portion 111a exposed to the exterior at the time of use of the needle assembly 101, and a small diameter portion 111b provided at the forward end of the large diameter portion 111a; on the outer peripheral surfaces of the large diameter portion 111a and the small diameter portion 111b, there are formed flat surfaces 111c at opposing positions.

Also, a protrusion 111d toward the outside is formed on each flat surface 111c of the small diameter portion 111b, and an inclined surface is formed in front of each protrusion 111d.

Further, the inner peripheral surface of the main body portion 111 has, at the rear of the bottom portion 112, a screw portion threadedly engaged with the cartridge, and, in front of the bottom portion 112, substantially wedge-shaped grooves 111e constituting the guide means G at opposing positions.

The cylindrical portion 106 is equipped with a flange 131 formed at the forward end and swollen on the inner peripheral side, two flat surfaces 132 formed on the outer peripheral surface at opposing positions, engagement holes 132a formed in the flat surfaces 132, and two through-holes 133 formed at positions attained through rotation by approximately 70° with respect to the flat surfaces 111c.

On the inner peripheral surface of the cylindrical portion 106, there is formed a thin-walled portion (not shown) fit-engaged with the small diameter portion 111b of the hub 104, and, at opposing positions in front of the thin-walled portion with the cannula 103 therebetween, there are formed grooves 106a constituting the guide means G so as to extend in the longitudinal direction.

The flat surfaces 132 are formed so as to be linearly aligned with the flat surfaces 111c of the hub 104; by inserting the hub 104 into the cylindrical portion 106, the protrusion 111d of the hub 104 is fit-engaged with the engagement holes 132a, whereby the hub 104 and the cylindrical portion 106 are coupled together.

As shown in FIG. 9, when the hub 104 and the cylindrical portion 106 are coupled together, the guide means G is formed on the inner peripheral surface of the hub member composed of the hub 104 and the cylindrical portion 106.

More specifically, at the rear of the through-holes 133 and the grooves 106a formed in the cylindrical portion 106, there are situated grooves 111e formed in the inner peripheral surface of the hub 104.

The grooves 106a are formed at positions attained through rotation by a predetermined angle with respect to the through-holes 133, and the forward end portions of the grooves 106a are situated in front of the through-holes 133.

In the pre-use state, the grooves 106a constitute the pre-use retaining portion A retaining the engagement protrusion 124, and, in the post-use state, the through-holes 133 constitute the post-use retaining portion B engaged with the engagement protrusion 124, with a rotation prevention protrusion 134 being formed between the pre-use retaining portion A and the post-use retaining portion B.

The grooves 111e of the hub 104 are formed in conformity with the width of the grooves 106a of the cylindrical portion 106 and the width of the through-holes 133; there is formed an inclined surface 114a inclined backwards from the pre-use retaining portion A side toward the post-use retaining portion B side, and, at the same time, a return prevention protrusion 135 is formed at the rear of the rotation prevention protrusion 134.

A method of using the needle assembly 101 constructed as described above will be illustrated; FIG. 9(a) shows the pre-use state of the needle assembly 101; the engagement protrusion 124 of the protective cover 107 is situated at the pre-use retaining portion A, and the cannula 103 is surrounded by the protective cover 107.

At this time, the engagement protrusion 124 is prevented from rotating to the post-use retaining portion B side by the rotation prevention protrusion 134.

Next, in the state of FIG. 9(a), the user presses the syringe substantially vertically against the skin of the patient while grasping the cylindrical portion 106; then, the protective cover 107 retracts, and the forward end of the cannula 103 is somewhat exposed as shown in FIG. 9(b), with the engagement protrusion 124 abutting the inclined surface 114a from the front side to move obliquely backwards.

At this time, due to the formation of the inclined surface 122a at the boundary between the engagement portion 122 and the cover portion 121 of the protective cover 107, when the protective cover 107 retracts while rotating, the friction generated between it and the flange 131 of the cylindrical portion 106 is mitigated, making it possible to retract the protective cover 107 smoothly.

When, thereafter, the protective unit 105 retracts while rotating, the use state as shown in FIG. 9(c) is attained, and, at this time, the engagement protrusion 124 gets over the return protection protrusion 135.

Then, the user performs a predetermined operation on the cartridge and gives an insulin injection; when, thereafter, he retracts the syringe, the protective cover 107 is placed at the advanced position due to the urging force of the spring portion 108, and the post-use state as shown in FIG. 9(d) is attained.

At this time, the engagement protrusion 124 advances without rotating to reach the position of the through-hole 133 as the post-use retaining portion B, and protrudes to the exterior due to the elastic force of the deformation portion 123 to be engaged with the through-hole 133, thereby preventing retraction of the protective cover 107 afterward.

Here, the through-hole 133 is situated on the rear side of the groove 106a as the pre-use retaining portion A, so that, as compared with the pre-use state, the forward end of the protective cover 107 in the post-use state is situated more rearwards.

In this way, in the needle assembly 101 of the second embodiment, it is possible to give an insulin injection by completely the same operation as in the case of the needle assembly 1 of the first embodiment.

As in the case of the needle assembly 1 of the first embodiment, once the post-use state is attained, the engagement protrusion 124 of the protective cover 107 is immovably fixed in position by the through-hole 133, so that re-exposure of the cannula 3 is prevented, making it possible to prevent re-use of the needle assembly 101 and erroneous piercing.

Further, since the protective unit 105 is formed as an integral unit, it is possible to reduce the number of components as compared with the case of the conventional needle assembly using a metal spring, and to facilitate the assembly operation.

Further, by arranging the protective cover 107 and the spring portion 108 in series, the configuration obtained by coupling together the protective cover 107 and the spring portion 108 does not become complicated, thus making it possible to facilitate the integral formation and to reduce the size of the needle assembly 101.

When placing the needle assembly in the use state from the pre-use state, the engagement protrusion 124 of the protective cover 107 retracts while rotating due to the inclined surface 114a of the guide means G, and, when placing it in the post-use state from the use state, the protective cover 107 moves straight forwards due to the urging force of the spring portion 108, so that it is possible to prevent as much as possible the engagement protrusion 124 from returning to the pre-use retaining portion A after use.

Further, since the return prevention protrusion 135 is provided between the pre-use retaining portion A and the post-use retaining portion B, it is possible to prevent the engagement protrusion 124 from returning to the pre-use retaining portion A, making it possible to guide the engagement protrusion 124 to the post-use retaining portion B more reliably.

Next, while in the first and second embodiments the protective cover 7 is provided with the engagement protrusion 24, and the hub member is provided with the guide means G, it is also possible, conversely, to provide the protective cover 107 with the guide means G and to provide the hub member with the engagement protrusion.

Figure 10:
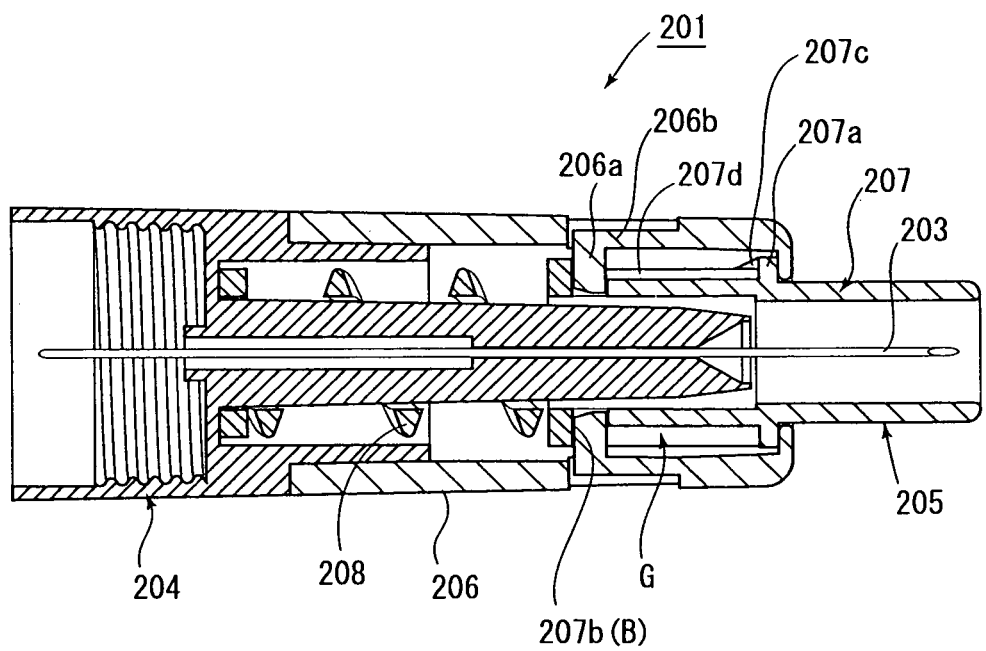
FIG. 10 A sectional view illustrating a needle assembly according to a third embodiment in the post-use state.

This will be described more specifically; FIG. 10 shows a needle assembly 201 according to the third embodiment in a post-use state; in the following description, the members common to those of the needle assembly 1 of the first embodiment are indicated by the same reference numerals with the number 200 added thereto.

As in the first embodiment, the needle assembly 201 is composed of a hub 204 retaining a cannula 203, a protective unit 205 advancing and retracting with respect to the hub 204 to surround the forward end of the cannula 203, and a cylindrical portion 206 coupled to the front side of the hub 204 and surrounding the outer periphery of the protective unit 204, with the hub 204 and the cylindrical portion 206 being coupled together to constitute a hub member.

As in the first embodiment, in the protective unit 205, a protective cover 207 and a spring portion 208 are formed integrally in series; further, a guide means G is formed on a side surface of an engagement portion 207a of the protective cover 207.

The cylindrical portion 206 constituting the hub member is provided with an engagement protrusion 206a protruding toward the inner peripheral surface; the engagement protrusion 206a is movable to the outer peripheral side due to a deformation portion 206b; in FIG. 8, the engagement protrusion 206a is engaged with a through-hole 207b as a post-use retaining portion B formed on the engagement portion 207a of the protective cover 207 to prevent the protective cover 207 from retracting.

The guide means G is provided with a pre-use retaining portion A (not shown) at a position adjacent to the post-use retaining portion B; in front of the post-use retaining portion B and the pre-use retaining portion A, there is formed an inclined surface 207c inclined from the pre-use retaining portion A side toward the post-use retaining portion B side.

Further, between the post-use retaining portion B and the pre-use retaining portion A, there are formed a rotation prevention protrusion (not shown) and a return prevention protrusion 207d.

Due to this construction, when the protective cover 207 is retracted from the pre-use state, the guide means G is moved backwards with respect to the engagement protrusion 206a of the cylindrical portion 206, and the inclined surface 207c abuts the engagement protrusion 206a.

After this, the inclined surface 207c abuts the engagement protrusion 206a, whereby the protective cover 207 retracts while rotating, and the use state is attained in which the cannula 203 protrudes; at this time, the engagement protrusion 206a gets over the return prevention protrusion 207d.

When the protective cover 207 advances from the use state, the guide means G moves forwards with respect to the engagement protrusion 206a, and the engagement protrusion 206a is engaged with the through-hole 207b as the post-use retaining portion B, so that the protective cover 27 is placed in the post-use state.

In this way, as in the case of the needle assembly 1 of the first embodiment, also in the needle assembly 201 of the third embodiment, once it is placed in the post-use state, the engagement protrusion 206a of the cylindrical portion 206 is immovably fixed in position by the through-hole 207b, so that re-exposure of the cannula 203 is prevented, making it possible to prevent re-use of the needle assembly 201 and erroneous piercing.

Further, since the protective unit 205 is formed integrally, and the protective cover 207 and the spring portion 208 are arranged in series, it is possible, as compared with the conventional needle assembly, to reduce the number of components and to facilitate the integral formation, making it possible to reduce the size of the needle assembly.

When placing the needle assembly in the use state from the pre-use state, the protective cover 207 retracts while rotating through engagement of the engagement protrusion 206a of the cylindrical portion 206 and the inclines surface 207c; and, when placing it in the post-use state from the use state, the protective cover 207 moves straight forwards due to the urging force of the spring portion 208, so that it is possible to prevent, as much as possible, the engagement protrusion 206a from returning to the pre-use retaining portion A.

Further, since the return prevention protrusion 207d is provided between the pre-use retaining portion A and the through-hole 207b, it is possible to prevent the engagement protrusion 206a from returning to the pre-use retaining portion A, making it possible to guide the engagement protrusion 206a to the through-hole 207b more reliably.

DESCRIPTION OF REFERENCE NUMERALS AND SIGNS

| 1 | needle assembly | 3 | cannula |
|---|---|---|---|
| 4 | hub | 5 | protective unit |
| 6 | cylindrical portion | 7 | protective cover |
| 8 | spring portion | 14a | inclined surface |
| 24 | engagement protrusion | 33 | through-hole |
| 35 | return prevention protrusion | | |
| A | pre-use retaining portion | | |
| B | post-use retaining portion | | |
| G | guide means | | |

The invention claimed is:

1. A needle assembly comprising: a hub retaining a cannula; a protective cover advancing and retracting with respect to the hub to be situated at an advanced position where it surrounds a forward end of the cannula and a retracted position where it exposes the forward end of the cannula; an urging means elastically provided between the hub and the protective cover and forwardly urging the protective cover; and a stopper means retaining the protective cover at the advanced position, the protective cover capable of being moved into a pre-use state in which the protective cover is situated at the advanced position to surround the forward end of the cannula, a use state in which the protective cover is situated at the retracted position to expose the forward end of the cannula, and a post-use state in which the protective cover is situated again at the advanced position to surround the forward end of the cannula and fixed in position so as not to be allowed to move to the retracted position again, the hub being provided with a cylindrical portion surrounding an outer periphery of the protective cover, one of a hub member formed by the hub and the cylindrical member and the protective cover being provided with an engagement protrusion, the other being provided with a guide means for regulating movement of the engagement protrusion, the guide means being provided with a pre-use retaining portion which retains the engagement protrusion at the position of the pre-use state and a post-use retaining portion for fixing the engagement protrusion at the position of the post-use state such that, when the protective cover is caused to retract against the urging force of the urging means from the pre-use state, the protective cover retracts to be placed in the use state, and when the protective cover is caused to advance from the use state, the engagement protrusion is fixed to the post-use retaining portion to be placed in the post-use state, and a step portion is provided on a path through which the engagement protrusion moves from the pre-use retaining portion to the post-use retaining portion such that when the protective cover moves from the pre-use state to the use state, if the engagement protrusion moves over the step portion, movement of the engagement protrusion toward the pre-use retaining portion side is regulated by the step portion wherein a return prevention protrusion protruding on an inner peripheral surface side is formed adjacent to the step portion, wherein a return prevention protrusion protruding on an inner peripheral surface side is formed adjacent to the step portion.

2. The needle assembly according to claim 1, wherein the engagement protrusion is provided on the protective cover, the guide means is formed in the hub member, the hub member is configured to have the cylindrical portion attached to a cylindrical base portion formed in the hub, the stopper means is formed by an engagement surface formed to extend toward the front side of the protective cover and a surface to be engaged with is formed to extend toward the rear side of the cylindrical portion, and the engagement surface abuts the surface to be engaged with from behind, whereby the protective cover is retained at the advanced position.

3. The needle assembly according to claim 2, wherein the pre-use retaining portion and the post-use retaining portion are formed on the cylindrical portion and the hub is provided with a guide portion having an inclined surface engaged with the engagement protrusion, the hub and the cylindrical portion being fit-engaged with each other to thereby provide the guide means.

4. The needle assembly according to claim 1, wherein the return prevention protrusion is inclined to gradually protrude from the pre-use retaining portion side toward the post-use retaining portion side.

5. The needle assembly according to claim 4, wherein a through-hole is formed at the position of the post-use retaining portion and, when the engagement protrusion of the protective cover is inserted into the through-hole, the engagement protrusion and the through-hole engage with each other to immovably fix the engagement protrusion in position by virtue of the through-hole.

6. The needle assembly according to claim 5, wherein the return prevention protrusion is formed in the hub.

7. The needle assembly according to claim 5, wherein the return prevention protrusion is formed in the cylindrical portion.

* * * * *